(12) United States Patent
Boulet et al.

(10) Patent No.: US 11,723,938 B2
(45) Date of Patent: *Aug. 15, 2023

(54) THYLAKOID EXTRACT COMPOSITION AND FORMULATION FOR THE TREATMENT OF INFLAMMATORY BOWEL DISEASE

(71) Applicant: Groupe Santé Devonian Inc., Montmagny (CA)

(72) Inventors: André P. Boulet, Quebec (CA); Theophilus J. Gana, Leesburg, VA (US); Nathalie Boucher, Trois-Rivieres (CA)

(73) Assignee: Groupe Santé Devonian Inc., Montmagny (CA)

( * ) Notice: Subject to any disclaimer, the term of this patent is extended or adjusted under 35 U.S.C. 154(b) by 199 days.

This patent is subject to a terminal disclaimer.

(21) Appl. No.: 16/998,004

(22) Filed: Aug. 20, 2020

(65) Prior Publication Data

US 2021/0128659 A1 May 6, 2021

Related U.S. Application Data

(63) Continuation of application No. 15/772,155, filed as application No. PCT/CA2016/051268 on Nov. 2, 2016, now Pat. No. 10,786,538.

(Continued)

(51) Int. Cl.
*A61K 36/00* (2006.01)
*A61K 36/21* (2006.01)
(Continued)

(52) U.S. Cl.
CPC ............ *A61K 36/21* (2013.01); *A61K 9/0031* (2013.01); *A61K 9/0053* (2013.01); *A61K 9/02* (2013.01); *A61K 9/08* (2013.01); *A61K 9/19* (2013.01); *A61K 31/015* (2013.01); *A61K 31/065* (2013.01); *A61K 31/409* (2013.01); *A61K 31/555* (2013.01); *A61K 47/06* (2013.01); *A61K 47/10* (2013.01); *A61K 47/14* (2013.01);
(Continued)

(58) Field of Classification Search
CPC ....................................................... A61K 36/00
See application file for complete search history.

(56) References Cited

U.S. PATENT DOCUMENTS

2005/0048148 A1 3/2005 Anderson et al.

FOREIGN PATENT DOCUMENTS

WO 03/004042 A1 1/2003

OTHER PUBLICATIONS

PCT International Search Report and Written Opinion for PCT Application No. PCT/CA2016/051268 dated Feb. 17, 2017 (12 pages).

(Continued)

*Primary Examiner* — Rosanne Kosson
(74) *Attorney, Agent, or Firm* — Eversheds Sutherland (US) LLP

(57) ABSTRACT

Use of a functional thylakoid extract, particularly in admixture with a physiologically acceptable carrier, in pharmaceutical application, in the treatment of inflammatory bowel disease, and method for the treatment thereof. The inflammatory bowel disease may comprise several diseases associated with inflammation of the small intestine, large intestine (colon), rectum or anus (anal sphincter), and may be particularly selected from ulcerative colitis and Crohn's disease.

9 Claims, 11 Drawing Sheets

Related U.S. Application Data

(60) Provisional application No. 62/250,023, filed on Nov. 3, 2015.

(51) Int. Cl.
| | | |
|---|---|---|
| *A61K 9/00* | (2006.01) | |
| *A61K 9/19* | (2006.01) | |
| *A61K 31/015* | (2006.01) | |
| *A61K 31/409* | (2006.01) | |
| *A61K 31/555* | (2006.01) | |
| *A61K 31/065* | (2006.01) | |
| *A61P 1/00* | (2006.01) | |
| *A61K 9/02* | (2006.01) | |
| *A61K 9/08* | (2006.01) | |
| *A61K 47/06* | (2006.01) | |
| *A61K 47/10* | (2017.01) | |
| *A61K 47/14* | (2017.01) | |
| *A61K 47/26* | (2006.01) | |
| *A61M 31/00* | (2006.01) | |

(52) U.S. Cl.
CPC ............ *A61K 47/26* (2013.01); *A61M 31/00* (2013.01); *A61P 1/00* (2018.01); *A61K 9/0056* (2013.01); *A61M 2210/1064* (2013.01)

(56) References Cited

OTHER PUBLICATIONS

Otari et al., "Protective Effect of Aqueous Extract of Spinacia Oleracea Leaves in Experimental Paradigms of Inflammatory Bowel Disease," Inflammopharmacology, 2012, 20:277-287.

Montelius et al., "Chloroplast Thylakoids Reduce Glucose Uptake and Decrease Intestinal Macromolecular Permeability," British Journal of Nutrition, 2011, 106:836-844.

Richardson GMP Limited, "Preliminary Prospectus for Orletto Capital Inc. (to be named 'Devonian Health Group Inc.')," 2016, http://groupedevonian.com/en/wp-content/uploads/2016/11/PRELIMINARYPROSPECTUS-1.pdf, pp. 45-80.

Vermeire et al., "C-reactive protein as a marker for inflammatory bowel disease," Inflamm Bowel Dis 10(5) :661-665, 2004.

Sands et al., "The role of TN Fa in ulcerative colitis," J Clin Pharmacol 47:930-941, 2007.

THYLAKOID EXTRACT COMPOSITION AND FORMULATION FOR THE TREATMENT OF INFLAMMATORY BOWEL DISEASE

CROSS REFERENCE TO RELATED APPLICATIONS

This application is a continuation application of U.S. application Ser. No. 15/772,155, filed Apr. 30, 2018, which claims the priority benefit of PCT/CA2016/051268 filed on Nov. 2, 2016, and which claims priority benefit of U.S. Provisional Application No. 62/250,023 filed Nov. 3, 2015. The entire contents of which are hereby incorporated by reference herein.

FIELD

This invention relates to a composition comprising functional thylakoids, in specific formulations that ensure the integrity and stability of the thylakoids (i.e. functional thylakoid extract), and methods of use to treat inflammatory bowel disease.

BACKGROUND

Inflammation is a process well known for its implication in acute and chronic diseases and disorders in the biomedical field. Although inflammation is a natural process associated with cell and tissue defense and regeneration, disorganized inflammation can contribute to (or is implicated in) many processes that are harmful to cells and tissues.

Inflammation is the body's reaction to infectious agents, antigen challenge or physical, chemical or traumatic injury. The main purpose of inflammation is to bring fluids, proteins, and cells from the blood into the damaged tissues. The main features of the inflammatory response are (i) vasodilation (widening of the blood vessels to increase blood flow); (ii) increased vascular permeability that allows diffusible components to enter the tissues; (iii) cellular infiltration by chemotaxis, or directed movement of inflammatory cells through the walls of blood vessels into the site of injury; (iv) changes in biosynthetic, metabolic, and catabolic profiles of the affected tissues; and (v) activation of cells of the immune system as well as enzymatic systems of the blood plasma.

In general, the inflammatory response is quite efficient in managing and repairing damages induced by injury or infectious agents. The degree to which these phenomena occur is normally proportional to the severity of the injury or the extent of the challenge. However, inflammation can become harmful to tissues when it develops in a disorganized, disproportionate or undesired manner and can lead to chronic disease or disorder.

Chronic inflammatory reaction may be seen as a long-lasting inflammation, where the inflammatory agent is continually present. However, chronic inflammation is often seen in cases where the inflammatory agent is not present, as is the case for inflammatory bowel disease. In this case, one or more inflammatory components contribute to the etiology and perpetuation of inflammation.

Though anti-inflammatory drugs are widely used to effectively treat inflammation, side effects of anti-inflammatory drug use, such as steroid resistance, high doses, osteoporosis, catabolism of proteins and lipids, redistribution of lipidic masse, etc. are a major concern in medical research and drug development.

WO 01/49305 discloses anti-oxidative compositions and method for their extraction. WO 03/04042 discloses their use in combination with other anti-inflammatory compounds. WO 2005/027944 discloses an oral formulation for the administration as anti-inflammatory compounds.

However, there is still a need to develop new compositions and formulations for the treatment chronic inflammation, particularly inflammatory bowel disease, that provide efficient relief from symptoms while avoiding side effects from common anti-inflammatory treatments.

SUMMARY

Therefore, there is provided a composition (named herein Composition A), comprising a functional thylakoid extract, a pharmaceutical formulation and its use in the treatment of inflammatory bowel disease.

In a first aspect, there is provided a composition to treat inflammatory bowel disease (IBD) in a subject, the composition comprising an effective amount of a functional thylakoid extract, particularly in admixture with a physiologically acceptable carrier.

In a second aspect, there is provided use of a thylakoid extract in the manufacture of a medication for treating inflammatory bowel disease (IBD) in a subject.

In a further aspect, there is provided use of a thylakoid for treating inflammatory bowel disease (IBD) in a subject.

In an alternative aspect, there is provided a formulation for the oral treatment of inflammatory bowel disease, comprising a thylakoid extract, in admixture with an orally-acceptable excipient, and optionally a preservative.

In an alternative aspect, there is provided a formulation for the intra-rectal treatment of inflammatory bowel disease, comprising a thylakoid extract, in admixture with a thickener in a physiological saline solution, and optionally a preservative.

In a further aspect, there is also provided a method for treating inflammatory bowel disease (IBD) in a subject in need thereof, comprising administering to said subject an effective amount of a thylakoid extract, optionally in admixture with a physiologically acceptable carrier.

In an alternative aspect, there is provided a kit for the production of a rectal enema for the treatment of inflammatory bowel disease, said kit comprising: a container comprising a thylakoid extract; a container comprising a rectal enema solution; and instructions on how to dissolve, suspend or dilute said extract in said solution.

Other objects, advantages and features of the present invention will become more apparent upon reading of the following non-restrictive description of preferred embodiments thereof, given by way of example only with reference to the accompanying drawings.

The contents of the documents cited in the present disclosure are incorporated by reference thereto.

DETAILED DESCRIPTION OF THE INVENTION

Abbreviations and Definitions

Definitions

Figure 1:
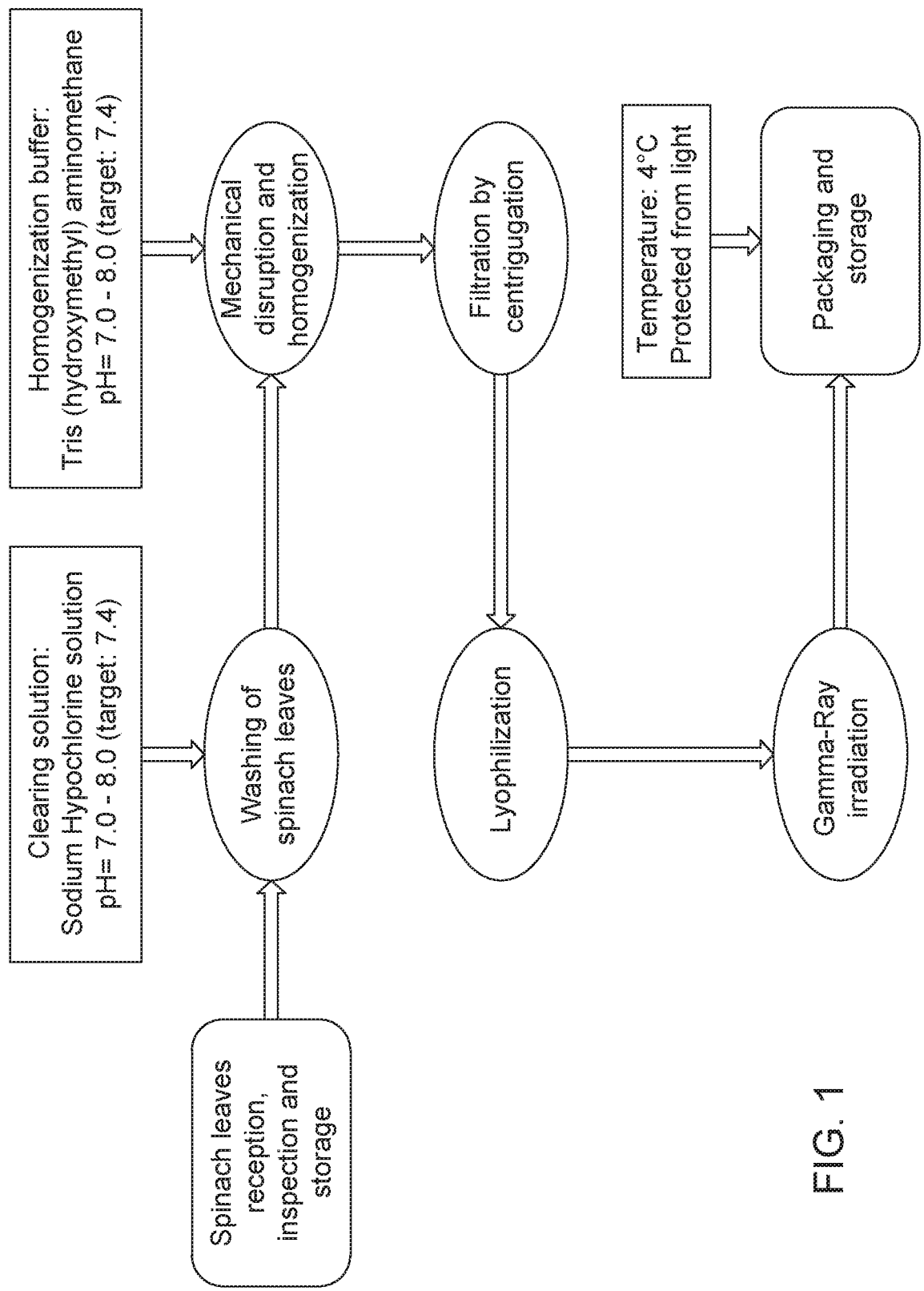
FIG. 1. Flow-diagram of composition A manufacturing process.

The term "about" as used herein refers to a margin of + or −10% of the number indicated. For the sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The terms "thylakoid", "thylakoid extract", "functional thylakoid extract" or "functional thylakoid" as used herein, means purified functional photosynthetic pigments in a thylakoid membrane environment (i.e. in an integral native state such that they can still be active or activated), particularly their original thylakoid environment. More particularly, these terms refer to functional thylakoid membranes as extracted by the process herein described and/or by the procedure disclosed in Bissonnette et al. (2004) or WO200149305.

Particularly, in connection with an aspect of the present thylakoid extract, the functional quality of the molecular complex can be measured by fluorescence based on its capacity to react to light and dissipate its energy ($F_v/F_m$ ratio), as is well known in the art and/or described in Maxwell (2000).

Detailed Description of Particular Embodiments

Composition

In accordance with a first aspect, the invention describes a composition to treat inflammatory bowel disease (IBD) in a subject, comprising an effective amount of an active thylakoid extract, particularly in admixture with a physiologically acceptable carrier. Particularly, the thylakoid extract is a spinach thylakoid extract, and more particularly extracted from spinach leaves.

Particularly the composition comprises purified functional photosynthetic pigments in a thylakoid membrane environment. Still particularly, the extract is quiescent and can be activated photosynthetically. More particularly, the extract is stabilized in its fundamental state (i.e. stable) by being devoid of any electron donor (such as water).

Most particularly, the composition is called Composition A and is defined as a raw organic spinach, active thylakoid extract, wherein the ratio chlorophyll a to total pigment is at least 0.4, particularly at least 0.5, more particularly at least 0.6.

In particular, the pigment comprised in the thylakoid extract is selected from the group consisting of: chlorophyll a, chlorophyll b, and carotenoids. More particularly, the pigment comprised in the thylakoid extract is selected from the group consisting of: chlorophyll a, chlorophyll b, lutein, and optionally, β-carotene and/or pheophytin. Still, most particularly, the pigment comprised in the thylakoid extract consists essentially of: chlorophyll a (more than 40%), followed by chlorophyll b (about 10-15%), lutein (about 10% or less), β-carotene (about 3%) and pheophytin (less than 1%).

Stabilized Extract

Particularly, the extract is stabilized in its fundamental state (i.e. stable) by being devoid of any electron donor (such as water). More particularly, the extract is stabilized by not containing more than 10% of water (or other electron donor).

The composition may be in powder form, such as a lyophilized dried composition, or may be admixed with physiologically-acceptable solid or liquid excipients, such as: PEG or DMSO to form a stabilized solution of suspension, inasmuch as the composition remains free, or substantially free, of electron donors (such as water), to maintain activity of the functional pigments.

Particularly, the stabilized extract is in solid form, more as particularly, as a powder. Still, more particularly, the extract is in powder form with at least 25 mg pigments per gram of powder. More particularly, the raw powder may be compressed in tablets, encapsulated, or packaged into aliquot packets or pouches. Alternatively, the powder may be mixed with suppository excipients and molded to form suppositories.

Alternatively, the stabilized extract is in liquid form, such as solution or suspension, in a liquid excipient devoid of water or electron donor, such as for example, PEG or DMSO. Particularly, the stabilized solution or suspension may be diluted in a liquid shortly or immediately before administration. Most particularly, for oral administration, the liquid may be water, juice, syrup, etc. Alternatively, for rectal administration, the liquid may be an enema formulation.

Uses

In accordance with a particular aspect, there is provided use of a thylakoid extract comprising purified functional photosynthetic pigments in a thylakoid membrane environment in the making of a medication for treating inflammatory bowel disease (IBD) in a subject.

Alternatively, there is provided use of a thylakoid extract comprising purified functional photosynthetic pigments in a thylakoid membrane environment for treating inflammatory bowel disease (IBD) in a subject.

Particularly, the use of the composition A are provided in the context where the IBD is selected from: ulcerative colitis (including proctitis) or Crohn's disease, more particularly in the context of using it for the treatment of ulcerative colitis (including proctitis), most particularly against ulcerative colitis.

Method of Treatment

In accordance with a particular embodiment, there is provided a method for treating inflammatory bowel disease (IBD) in a subject in need thereof, comprising administering to the subject an effective amount of a thylakoid extract comprising purified functional photosynthetic pigments in a thylakoid membrane environment, particularly in admixture with a physiologically acceptable carrier.

Particularly, the method of treatment is provided in the context of treating: ulcerative colitis (including proctitis) or Crohn's disease, more particularly in the context of treating ulcerative colitis.

Therapeutic Indications

Particularly, the inflammatory bowel disease may comprise several diseases associated with inflammation of the small intestine, large intestine (colon), rectum or anus (anal sphincter), and may particularly include: ulcerative colitis and Crohn's disease, including proctitis in both cases.

In accordance with a particular aspect, there is provided the thylakoid extract of the invention for use or for the treatment of proctitis that is provoked by other causes than IBD, such as for example, radiation proctitis or infective proctitis.

Subjects

In particular, the present use and method may be indicated for the treatment of mammalian subjects, particularly pets or human, more particularly cats, dogs, horses, or human, most particularly humans.

Dosage

As used herein, the terms "effective amount" means a dose sufficient to induce a reduction in IBD symptoms or a reduction in markers of inflammation, and may be dependent on the subject being treated, the history of disease and/or the severity of symptoms.

In accordance with a particular embodiment, the extracts comprises an effective amount of about 0.00005 to 500 mg per Kg of subject's body weight, more particularly from about 0.05 to 10 mg per Kg of subject's body weight.

In accordance with a particular embodiment, the extract is provided at a dosage between about 150 to about 2000 mg/day; more particularly about 250, about 375, about 500, about 750, about 1000 or about 1500 mg/day; most particularly, 250, 500 or 1000 mg/day.

Formulation

In accordance with a particular aspect, there is provided the use or the method of treatment as defined herein, wherein the composition is formulated for oral or intra-rectal administration, more particularly intra-rectal administration such as an enema or a suppository.

In accordance with a particular aspect, there is provided an enema formulation for the use or treatment of inflammatory bowel disease, comprising a composition comprising purified functional photosynthetic pigments in a thylakoid membrane environment, in admixture with a thickener, and optionally a preservative.

Particularly, the thickener is selected from: Xanthan gum and Carbopol®. Still particularly, the preservative is selected from: methylparaben; propylparaben; ethylparaben; and butylparaben. Most particularly, the preservative is dissolved in propylene glycol, and particularly, the pH is adjusted to about 6.5.

In accordance with a particular aspect, there is provided a formulation suitable for molding a suppository for the use or treatment of inflammatory bowel disease, comprising a thylakoid extract comprising purified functional photosynthetic pigments in a thylakoid membrane environment, in admixture with a rectally-acceptable excipient, and optionally a preservative.

According to a particular embodiment, a rectally-acceptable excipient may be selected from, but not limited to: cocoa butter, glycerin, semisynthetic glycerides, gelatin, polyoxyl 40 stearate (miscellaneous base), and PEG.

Kits

In an alternative aspect, there is provided a kit for the production of a rectal enema for the treatment of inflammatory bowel disease, said kit comprising: a container comprising a thylakoid extract comprising purified functional photosynthetic pigments in a thylakoid membrane environment in dried form, or in a stabilized solution or suspension); a container comprising a rectal enema solution; and instructions on how to dissolve, suspend or dilute said extract in said solution. Particularly, the kit optionally comprises a rectal bulb syringe, and instructions for intra-rectal administration of the thylakoid enema formulation.

In an alternative aspect, there is provided a kit for the production of a rectal enema for the treatment of inflammatory bowel disease, said kit comprising: a container comprising a stabilized thylakoid extract comprising purified functional photosynthetic pigments in a thylakoid membrane environment in dried or liquid form; a container comprising a rectal enema solution; and instructions on how to dissolve, suspend or dilute said extract in said enema solution. Particularly, the kit optionally comprises a rectal bulb syringe, and instructions for intra-rectal administration of the thylakoid suspension.

Particularly, the stabilized thylakoid extract is in the form of a powder. More particularly, the powder of thylakoid extract is in the form of a tablet, a capsule, or a single dose packet (or pouches) of about 250 mg, about 500 mg or about 1000 mg doses.

More particularly, the stabilized solution or suspension of thylakoid extract is in the form of aliquots (packets, pouches, ampoules, etc.), or in a bottle equipped with a dropper, particularly a metered dropper of about 250 mg, about 500 mg or about 1000 mg doses.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

EXAMPLES

Example 1—Preparation of Thylakoid Extract (Composition A)

Composition A originates from the mesophyll tissue of baby spinach (*Spinacia oleracea* L.) leaves, which is rich in chloroplasts. The inner membranes of the chloroplasts, organized in structures known as thylakoids, are extracted from baby spinach, concentrated and stabilized into a solid powder form. The major constituents of thylakoid membranes are pigments, proteins and lipids.

TABLE 1

| Physical appearance: | Dark green powder |
|---|---|
| Solubility in water: | Insoluble |
| Solubility in alkaline medium (pH 10.6) | 0.5 mg/mL |
| Solubility in acidic medium (pH 1.0) | 0.3 mg/mL |

Manufacturing Process

The manufacturing process for Composition A is presented schematically in the flow diagram of FIG. 1.

The processing steps are executed with minimum light exposure and under cool conditions to preserve a maximal activity of the photosynthetic pigments. The steps are carried out in the following order: inspection of spinach leaves and washing with a sodium hypochlorite solution; mechanical disruption and homogenization; filtration by centrifugation; lyophilisation; and gamma-ray irradiation.

Inspection of spinach leaves and washing with a sodium hypochlorite solution. After visual inspection is performed to verify dimensional and identity attributes (e.g. leaves are green without discoloured zones or yellowish pecks (chlorose)), spinach leaves are first washed at a fixed solution-to-leaves ratio (44 kg:5.4 kg) on a mass basis, with a sodium hypochlorite solution adjusted to a pH between 7.0 and 8.0 (target pH: 7.4) to reduce the microbial flora naturally found on the leaves of fresh produce.

Mechanical disruption and homogenization. After draining the excess sodium hypochlorite solution, leaves are transferred into a mechanical cutter/mixer along with a fixed volume of Tris (hydroxymethyl) aminomethane buffer solution at pH between 7.0 and 8.0 (target pH: 7.4) at a fixed solution-to-leaves ratio (5.4 kg:3.7 kg) on a mass basis. This step is used to cut and homogenize the leaves into a coarse suspension while freeing up fragments of the thylakoid membranes originating from chloroplasts.

Filtration by centrifugation. The suspension is then filtered in a basket centrifuge. The centrifugation is performed at a target speed of 3100 rpm (range: 2800-3200 rpm). This step allows the removal of fibres, debris and coarse material which are retained on a screen, yielding a by-product cake to be discarded. Composition A, the active ingredient, is found in the centrifugate and is collected and kept at a temperature below 10° C. for further processing.

Lyophilisation. The material is then distributed over shallow stainless steel plates and allowed to freeze in darkness at a temperature ≤−30° C. for a period of at least 2 hours. The plates kept at a target temperature of 10° C. are then transferred into a lyophilizer and the product is lyophilized.

Gamma-ray irradiation. A terminal gamma-ray irradiation step is carried out. After irradiation, Composition A is transferred into jars fitted with a tight screw cap.

Pigment Composition and Other Characteristics

Spinach contains natural antioxidants (e.g. flavonoids) and photosynthetic pigments (chlorophylls and carotenoids). The inner membranes of the chloroplasts are organized in structures known as thylakoids. The major constituents of thylakoid membranes are pigments, proteins and lipids.

Figure 2:
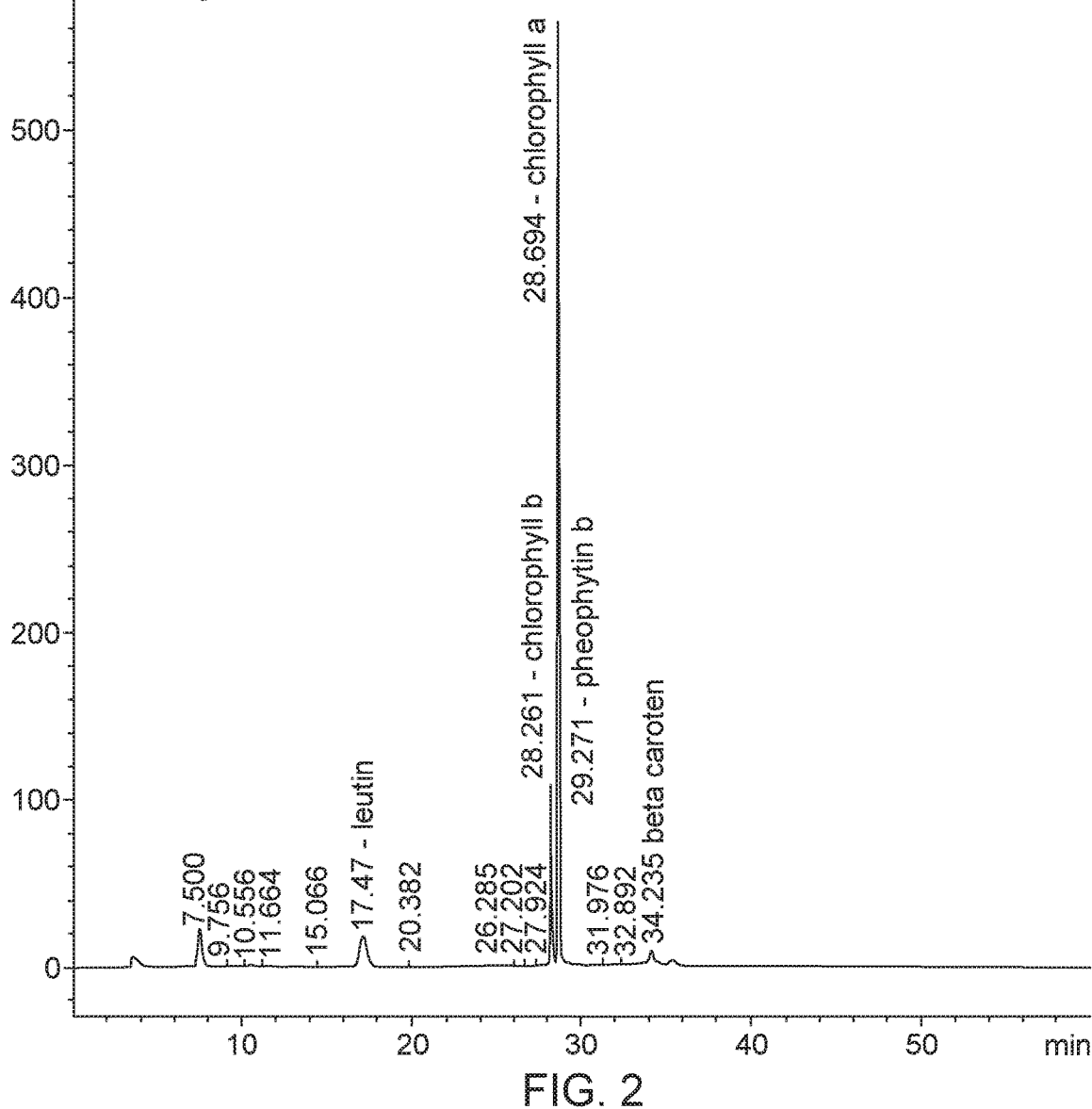
FIG. 2. HPLC chromatogram showing pigment profile of Composition A.
Figure 3A:
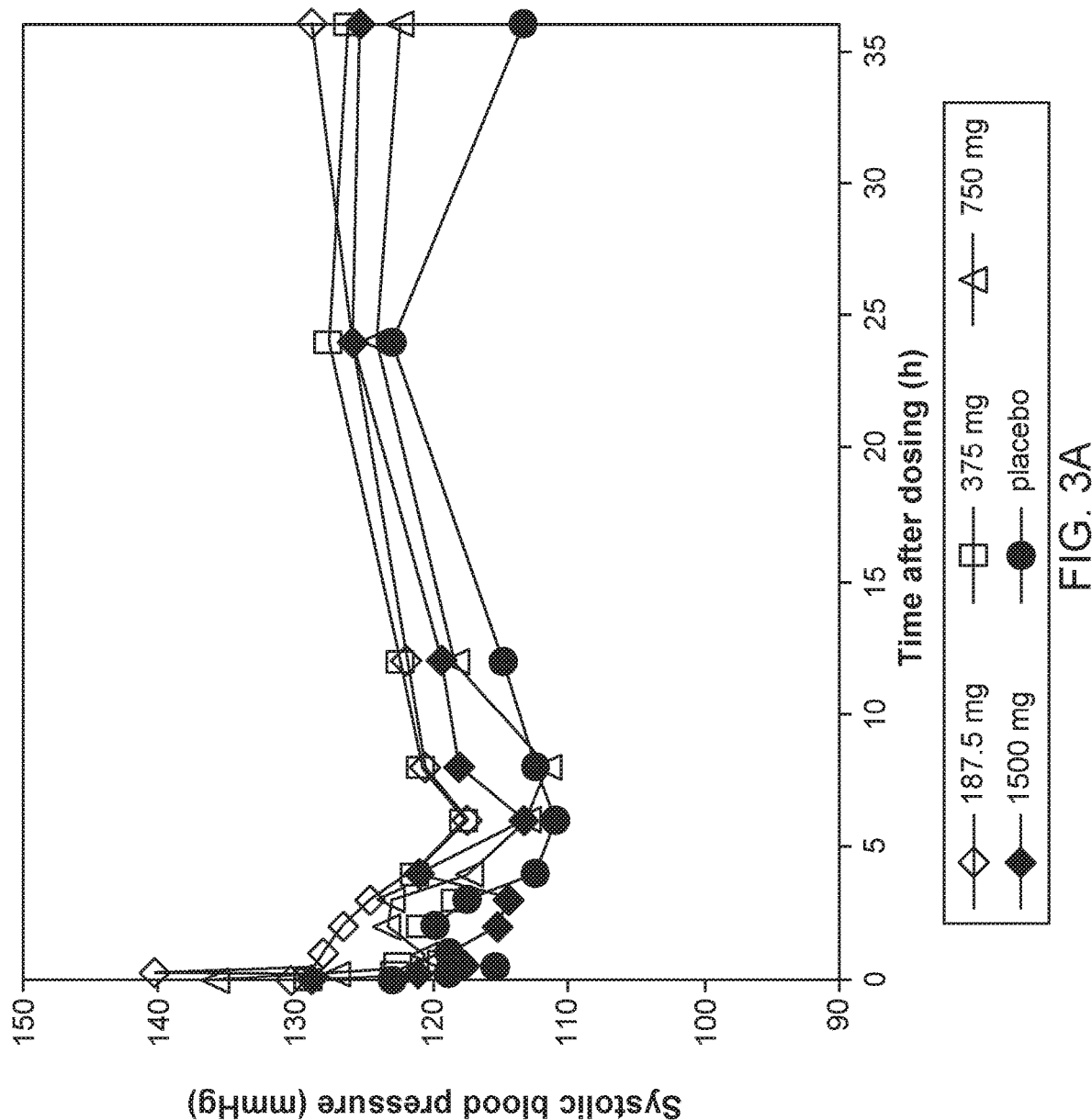
FIG. 3. Mean time course of vital signs up to 36 hrs after dosing (Safety population). A) systolic blood pressure, B) diastolic blood pressure, C) pulse rate, D) respiratory rate, E) body temperature.
Figure 3B:
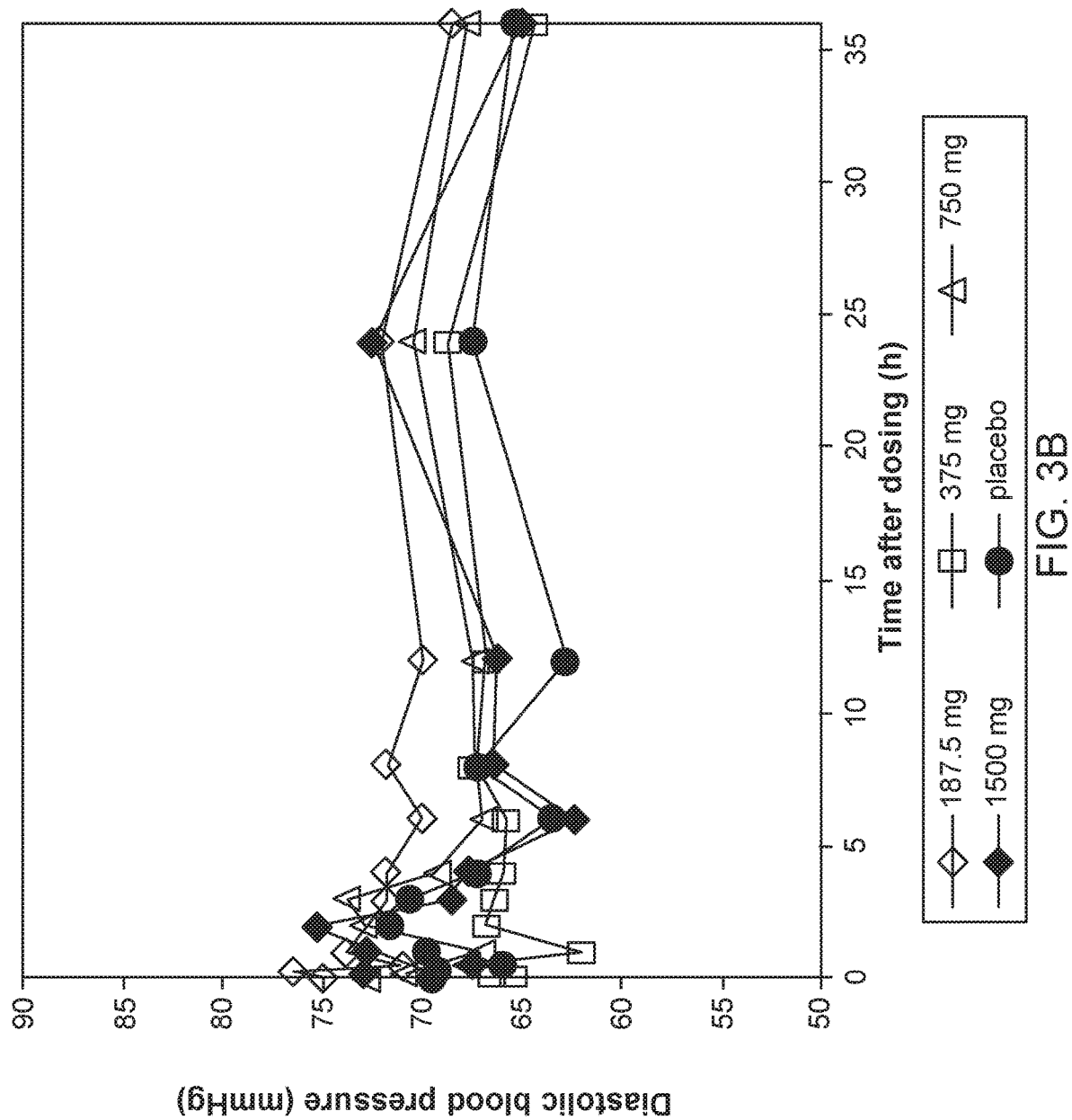
Figure 3C:
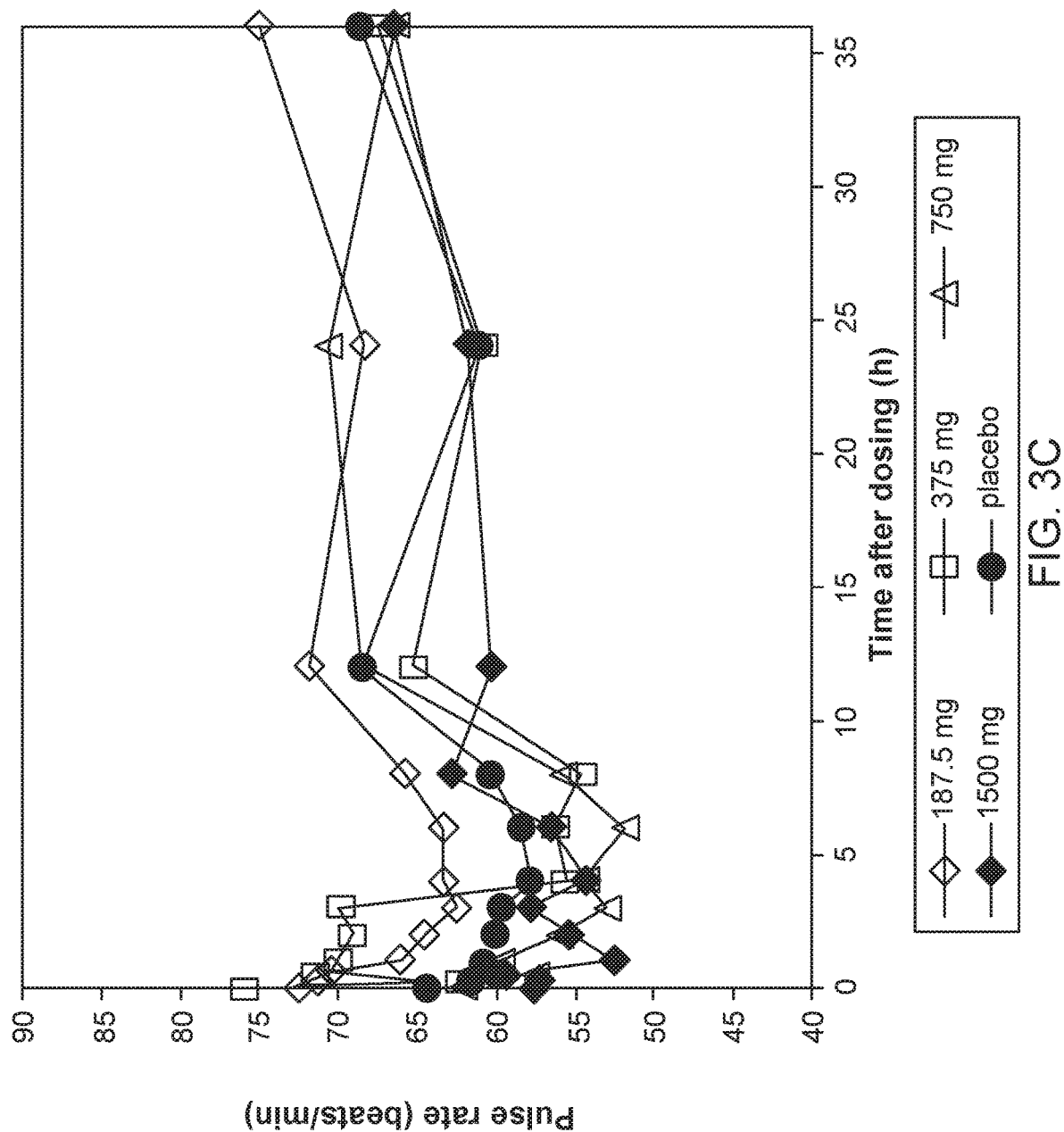
Figure 3D:
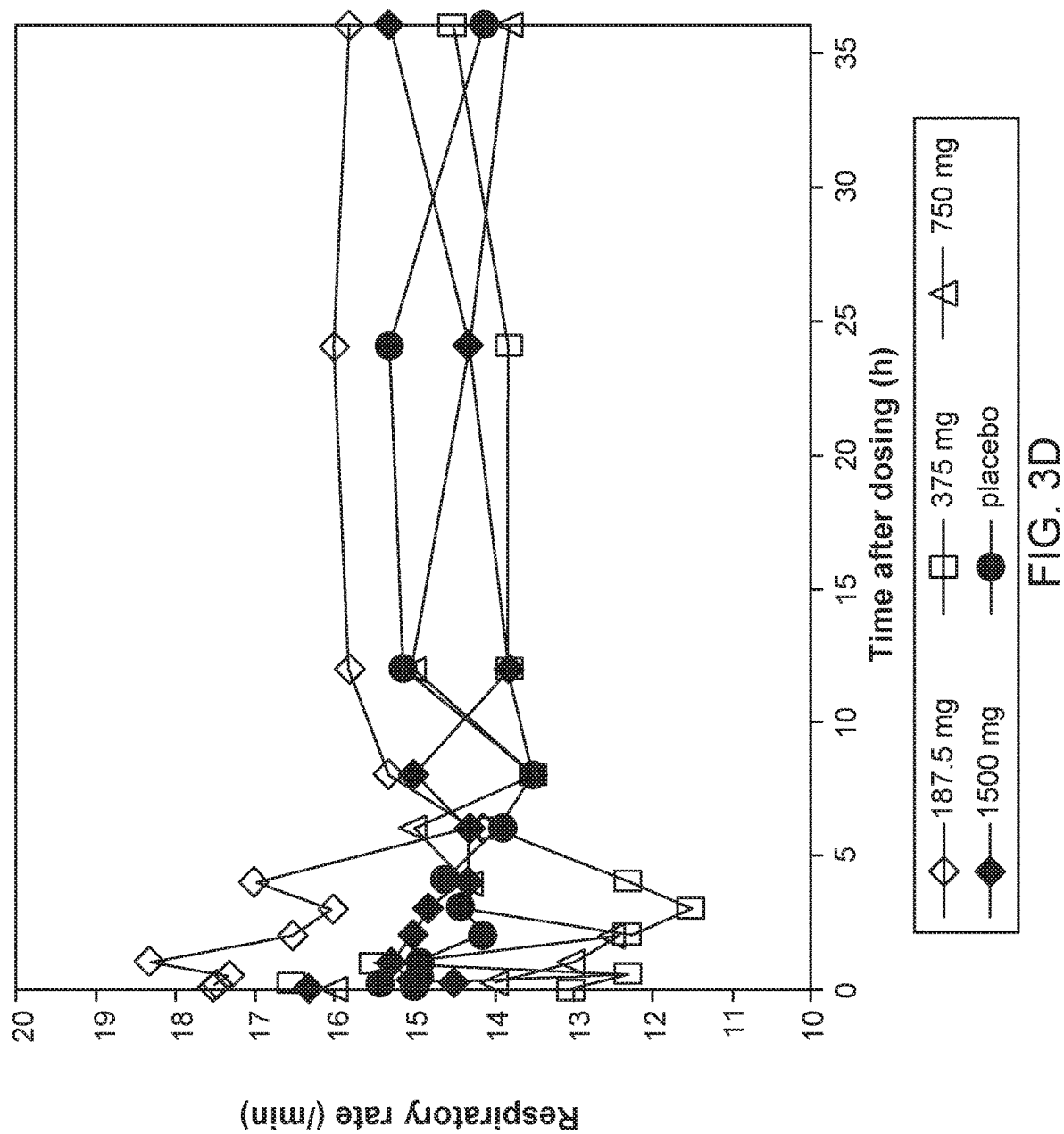
Figure 3E:
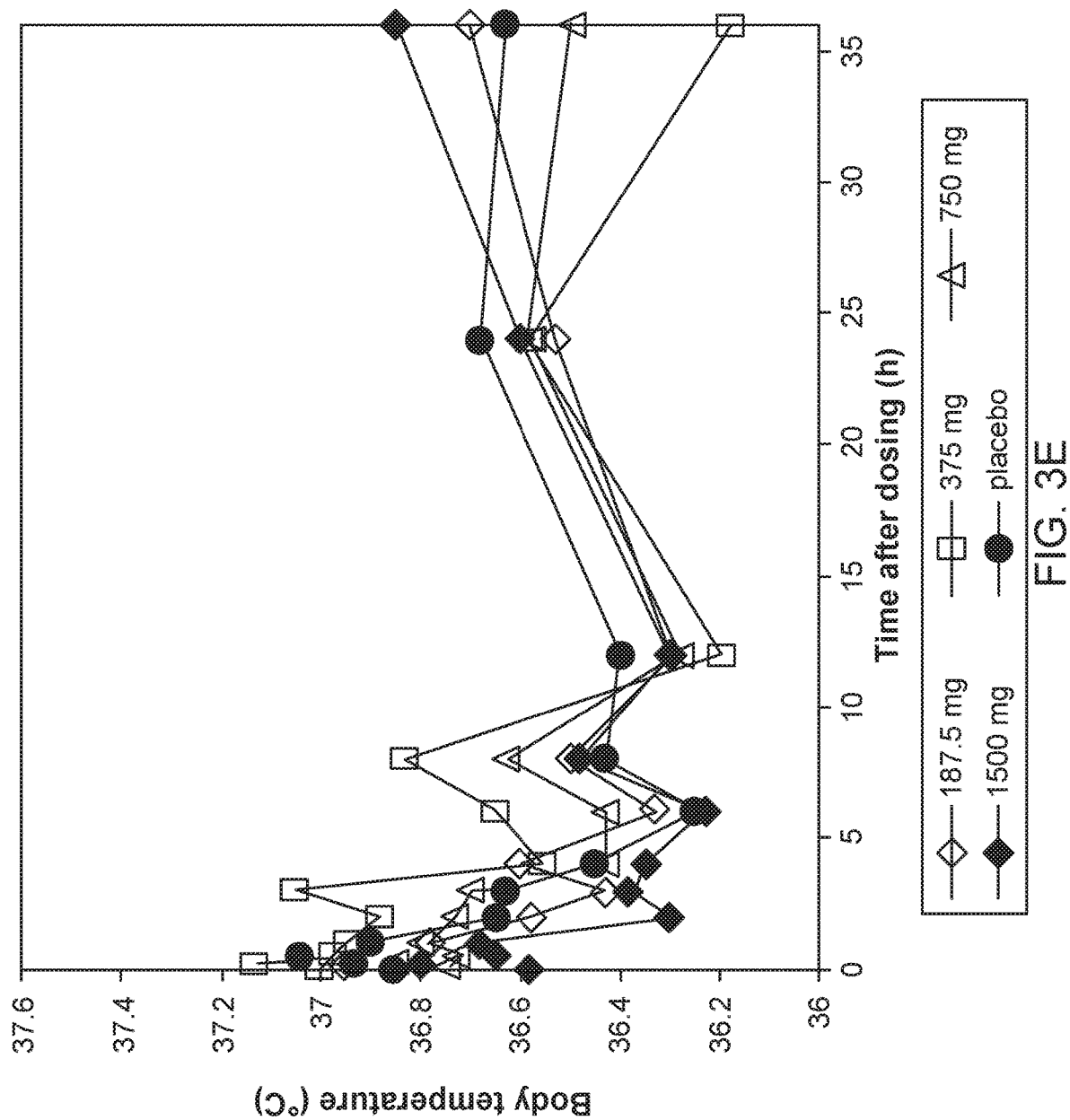

Composition A originates from the mesophyll tissue of spinach leaves which are rich in chloroplasts. To date, the following pigments have been identified in Composition A using HPLC analysis: lutein, chlorophyll b, chlorophyll a, pheophytin and β-carotene. A typical chromatogram showing the pigment profile of Composition A, in area %, is presented in FIG. 2. This analysis shows that the major constituent of Composition A is chlorophyll a (62.5%), followed by chlorophyll b (13.1%), lutein (9.4%), β-carotene (2.98%) and pheophytin (0.45%).

Preferably, raw baby spinach were used from a grower certified as per the National Organic Standards of the United States Department of Agriculture (USDA) to minimize risks of presence of potential chemical residues from fertilizers or pesticides in Composition A.

Justification of Specification

Composition A is characterized by its pigment content expressed in milligram of pigment per gram of powdered extract. Based on process capabilities and allowing for seasonal variability in the herbal starting material, a specification of not less than 25 mg pigment/g extract was set. Based on stability data, a limit of 80% of the initial pigment content was set for shelf-life.

Pigment profile also allows identification of the various pigments present in Composition A and their ratios in area percent. Given the profile determined in batches, it was established that chlorophyll a, chlorophyll b, lutein and β-carotene should be present and that the average ratio of chlorophyll a to total peak area response should not be less than 0.40.

Since water is used as extraction solvent in the manufacturing process, a test to determine water content in Composition A has been included. A specification of not more than 10% w/w of water was set to control moisture.

The safety of the impurity levels present in Phase 1 clinical batch was qualified in a combined intrarectal single dose and 14-day repeat dose toxicity study in minipigs. As shown in Table 2, similar impurity levels were present in Phase 2 clinical batch. The maximum dose administered in the repeat dose toxicity study (200 mg/kg) was 14-fold higher than the maximum Phase 2 clinical trial dose (1000 mg or 14.3 mg/kg), which was administered once a day for 14 days. No toxicity findings of toxicological significance were observed in this study. A NOAEL for the significant events was justifiably defined as 200 mg/kg on the basis of microscopic minimal tubular degeneration in the kidneys, which was consistent with previously reported spontaneously occurring microscopic lesions in the Gottingen minipig.

TABLE 2

SPECIFICATION FOR COMPOSITION A as a DRUG SUBSTANCE

| Test | Acceptance criteria |
|---|---|
| PHYSICAL/CHEMICAL TESTING | |
| Description | Dark green powder |
| Total Pigment Content (mg/g) | Not less than 25 mg/g |
| | End of shelf-life: NLT 80% of release content |

TABLE 2-continued

SPECIFICATION FOR COMPOSITION A as a DRUG SUBSTANCE

| Test | Acceptance criteria |
|---|---|
| Pigment Profile | |
| Lutein | Lutein, Chlorophyll a, chlorophyll b and β-carotene present |
| Chlorophyll b | |
| Chlorophyll a | Average of ratio of Chlorophyll a against total peak area response not less than 0.40 |
| Pheophytin b | |
| Beta carotene | |
| Unknown | |
| Tromethamine[a] Content (% w/w) | ≤5.0% w/w |
| Water Content (% w/w) | <10% w/w |
| Heavy Metals (μg/g) | ≤15% w/w |
| Residue on Ignition (%) | ≤5.0% |
| Cadmium (μg/g) | ≤15 μg/g |
| Chloride Content (%) | ≤1.5% |
| Pesticides Residues (mg/kg) | Below limit of detection in all cases |
| MICROBIOLOGICAL TESTING | |
| Aflatoxins | |
| $B_1$ | Not more than 2 ppb |
| $B_{1+}\ B_{2+}\ G_{1+}\ G_2$ | Not more than 4 ppb |
| Total Aerobic Microbial Count (CFU/g)[b] | $<1.0 \times 10^3$ |
| Yeasts and Moulds (CFU/g)[b] | $<1.0 \times 10^2$ |
| Total Anaerobic Sporulated Count (CFU/g)[c] | $<1.0 \times 10^1$ |
| Pathogens | |
| *Escherichia coli* | Negative for all species |
| *Staphylococcus aureus* | |
| *Salmonella* sp. | |
| *Pseudomonas aeruginosa* | |

[a]Tris (hydroxymethyl) aminomethane
[b]Method based on USP <61> Microbial Limit Test
[c]Laboratory procedure in the Compendium of Analytical Methods of the Canadian Health Protection Branch of Health Canada Stability To date, two batches of Composition A drug substance, packaged in a jar with a tight screw cap, have been placed on stability under the following conditions: 5° C.±3° C. (current recommended storage condition). The data available to date indicates that Composition A is stable after storage for at least 18 months under refrigerated conditions.

Example 2—Investigational Medicinal Product

Description and Composition of the Medicinal Product

The investigational medicinal product is a rectal enema which was reconstituted by patients prior to administration. The rectal enema was prepared by reconstituting Composition A drug substance or matching placebo powder with the reconstitution solution.

In order to do so, each patient received the following materials for each dose to be administered:
  One bottle containing 60 g of reconstitution solution; and
  One bottle containing either Composition A substance or matching placebo powder.

Three (3) doses of Composition A were administered in this study:
  250 mg of Composition A in 60 g of reconstitution solution;
  500 mg of Composition A in 60 g of reconstitution solution; or
  1000 mg of Composition A in 60 g of reconstitution solution.

The placebo rectal enema was composed of 500 mg of matching placebo powder reconstituted in 60 g of reconstitution solution. The composition of the reconstitution solution is presented in Table 3.

TABLE 3

| Ingredient | Quantity per unit (mg/60 g) | Quantity per unit (%) | Function |
|---|---|---|---|
| Propylene Glycol USP | 3,000.00 | 5.000 | Suspending agent |
| Sodium Chloride USP | 450.00 | 0.750 | Osmolarity adjustment |
| Xanthan Gum, NF | 366.00 | 0.610 | Viscosity agent |
| Carbopol ® 980, NF | 72.00 | 0.120 | Viscosity agent |
| Methylparaben NF | 9.84 | 0.016 | Preservative |
| Propylparaben NF | 1.83 | 0.003 | Preservative |
| Ethylparaben NF | 1.83 | 0.003 | Preservative |
| Butylparaben NF | 1.83 | 0.003 | Preservative |
| Hydrochloric Acid NF | — | — | pH adjustment |
| Sodium Hydroxide NF | — | — | pH adjustment |
| USP Purified Water | 56,096.67 | 93.495 | Suspending solvent |

The composition of the matching placebo powder is presented in Table 4.

TABLE 4

| Ingredient | Quantity per unit (mg/60 g) | Quantity per unit (%) | Function |
|---|---|---|---|
| XH2664 US Green 3 Shade* | 1.0 | 0.1 | Colorant |
| FD&C Yellow No 6 (E110) spray-dried | 3.1 | 0.3 | Colorant |
| Sucrose, NF | 829.9 | 83.0 | Bulking ingredient and cryoprotectant |
| Pregelatinized Corn Starch, NF | 166.0 | 16.6 | Bulking ingredient and moisture control |
| Purified Water, USP | Removed during lyophilization | | Lyophilization solvent |

*Contains FD & C Blue No 1 (E133) and FD & C Yellow No 5 (E102). The Certificate of Compliance with EC Directive 95/45/EC on Food Colours and the FAO/WHO specification can be found in Annex 4

The formula of the reconstitution solution was typical of retention rectal enemas and was composed of ingredients of suitable viscosity to ensure proper contact characteristics at the site of delivery. A preservative system composed of four parabens ensured that bioburden remained within acceptable limits. Sodium chloride was present to control osmolarity. The formula was slightly modified from the reconstitution solution used in the Phase 1 study in that Carbopol® 980 was added and the recommended storage changed from room temperature to refrigeration in order to maintain physical and chemical characteristics over a longer period of time. The batch formula for the reconstitution solution is presented in Table 5.

TABLE 5

| Ingredient | Quantity per batch (grams/80 kilograms) |
|---|---|
| Propylene Glycol USP | 4,000.00 |
| Sodium Chloride USP | 600.00 |
| Xanthan Gum, NF | 488.00 |
| Carbopol ® 980, NF | 96.00 |
| Methylparaben NF | 13.12 |
| Propylparaben NF | 2.44 |
| Ethylparaben NF | 2.44 |
| Butylparaben NF | 2.44 |
| Hydrochloric Acid NF | — |
| Sodium Hydroxide NF | — |
| USP Purified Water | 74,795.57 |

Also, a matching placebo powder was formulated for Composition A using sucrose and pregelatinized corn starch as bulking agents. Colorants were added to match the dark green colour of Composition A. This mixture was lyophilized to mimic the granular appearance of Composition A. Sucrose also acted as a cryoprotectant and pregelatinized corn starch prevented undue moisture pick-up upon storage. The batch formula for the matching placebo powder is presented in Table 6.

TABLE 6

| Ingredient | Quantity per batch (g/2 kg) |
|---|---|
| XH2664 US Green 3 Shade* | 2.0 |
| FD&C Yellow No6 (E110) spray-dried | 6.2 |
| Sucrose, NF | 1659.8 |
| Pregelatinized Corn Starch, NF | 332.0 |
| Purified Water, USP | Removed during lyophilization |

*Contains FD & C Blue No 1 (E133) and FD & C Yellow No 5 (E102). The Certificate of Compliance with EC Directive 95/45/EC on Food Colours and the FAO/WHO specification can be found in Annex 4

The batch formula for the rectal enema that was administered in the Phase 2a study is presented in Table 7.

TABLE 7

| | Dose of Composition A to be administered | | | |
|---|---|---|---|---|
| Ingredient | 0 mg | 250 mg | 500 mg | 1000 mg |
| Reconstitution Solution* | 60 g | 60 g | 60 g | 60 g |
| Comp. A drug substance | N/A | 250 mg | 500 mg | 1000 mg |
| Matching Placebo Powder** | 500 mg | N/A | N/A | N/A |

*See Table 5 for batch formula
**See Table 6 for batch formula

Reconstitution Solution 80 kg of reconstitution solution was prepared by pooling 4×20 kg bulk solutions. The manufacturing process for this preparation (20 kg bulk solutions and pooling) is presented below.

Step #1 Preparation of pH 2.5 USP Purified Water: 20 L Stainless steel vessel fitted with a mechanical stirrer was filled with 20 kg of USP Purified Water. A solution of HCl 1N was slowly added to the USP Purified Water under agitation to adjust the pH to 2.5±0.05.

Step #2 Preparation of the Xanthan Gum/Carbopol® Solution: A 20 L stainless steel double jacketed vessel fitted with a mechanical stirrer was filled with 11.1 kg of pH 2.5 USP Purified Water from Step #1 and the temperature was adjusted to 40° C. When the temperature reached 40° C., xanthan gum (122.0 g), sodium chloride (150.0 g) and Carbopol® 980 (24.0 g) were added and the solution was mixed at a speed of 800 rpm for 60 minutes.

Step #3 Preparation of the Preservatives Solution: A 1 L glass bottle containing 1000.0 g of propylene glycol was placed in a heated water bath to reach a temperature of 50° C. When the temperature reached 50° C., the 4 preservatives were added:
  Methylparaben: 3.28 g
  Propylparaben: 0.61 g
  Ethylparaben: 0.61 g
  Butylparaben: 0.61 g
and the solution was kept under agitation at a temperature of 50° C. until the above preservatives were dissolved.

Step #4 Preparation of the bulk solution: The Preservatives Solution from Step #3 was added while mixing to the 20 L stainless steel vessel containing the Xanthan Gum/Carbopol® Solution prepared in Step #2 and maintained at a temperature of 40° C. USP Purified Water pH 2.5, from Step #1, was added to the vessel in sufficient quantity to reach 20.0 kg of bulk solution. Heating was stopped and the bulk solution was allowed to cool under agitation for 60 minutes. When a temperature of 25° C. was reached, the pH was measured and if necessary, adjusted to 6.5±0.05 using either HCl 1N or NaOH 1N solutions.

Steps #1 to #4 were repeated three times to generate 3×20 kg of additional bulk solutions.

Before proceeding with pooling, a viscosity test was performed on each of the 20 kg bulk solutions. If viscosity was between 1000 and 1200 cps, pooling proceeded (step #5).

Step #6 Packaging of the reconstitution solution: Not less than 60 g of reconstitution solution was filled using a metered pump in bottles with a cap fitted with a cannula.

Matching Placebo Powder

Step #1 Preparation of the Colour Solution: This solution was prepared by adding 2 g of US Green 3 Shade and 6.2 g of FD&C Yellow No 6 in a tared 1 L beaker equipped with a magnetic stirrer containing 6657.8 g of USP Purified Water; this solution was kept under agitation at 200 rpm for 5 minutes.

Step #2 Preparation of the Bulk Powder Dispersion: 1659.8 g of sucrose and 332.0 g of pregelatinized starch were mixed together in a 5000 mL beaker. This mixture was then slowly transferred, under agitation at 800 rpm, into the colour solution prepared in Step #1 and agitation was maintained until complete dispersion.

Step #3 Lyophilization: The resulting bulk powder dispersion from step #2 was transferred into freeze drying trays and initially dried at −50° C. for 24 hours. The product was then freeze-dried.

Composition A Rectal Enema

For each dose to be administered, patients received 2 bottles: one bottle containing the reconstitution solution and one bottle containing Composition A active substance or matching placebo powder. These bottles were kept under refrigeration.

For reconstitution, patients removed the 2 bottles described above from the refrigerator and left them at room temperature for 2 hours. Patients then reconstituted the rectal enema by transferring the content of the bottle containing the reconstitution solution to the bottle containing the Composition A active substance or matching placebo powder. Patients self-administered the rectal enema within 1 hour from reconstitution. The reconstituted enema was shaken manually for at least 30 seconds immediately before administration.

Example 3—Pre-Clinical Results Summary

Preclinical Studies

Numerous preclinical studies have been conducted demonstrating the anti-inflammatory, antioxidative, and immunomodulatory properties of Composition A. The preclinical studies include: (i) in vitro and in vivo pharmacology studies; and (ii) safety pharmacology and toxicology studies, and are summarized in Tables 8 and 9 below.

TABLE 8

Summary of In Vitro and In Vivo Pharmacology Studies Conducted with Comp. A

| Title of Study | Formulation/Route | Results/Findings |
| --- | --- | --- |
| In Vitro Studies | | |
| Long-term Protection Against Lipid Peroxidation By Composition A in a Lipid Micelle Model In Vitro | N/A | Composition A significantly protected PLPC-Composition A micelles against lipid peroxidation with no apparent lag phase as seen with the classical anti-oxidants. (PLPC = 1-palmitoyl-2-linoleoyl-sn-glycro-3-phosphatidylchlorine) Anti-oxidative effect of Composition A was long-lasting, superior to that shown by Trolox over 24 hrs, and was maintained over 8 hrs while Trolox's was not. |
| Anti-oxidative Effect and Dose-Dependent Protection By Composition A of Hemolysis of Human and Bovine Erythrocytes Exposed to 1 to 3 mM tBHP | N/A | Composition A protected erythrocytes against hemolysis and lipid peroxidation in a dose-dependent manner. The greater the damage by ROS, the greater the protection by Composition A - as observed in the micelle model; and Composition A exhibited a long-lasting effect. |
| In Vitro Modulation of Cytokine Expression in Alveolar Macrophages (AM) by Composition A | N/A | Composition A pretreatment of lipopolysaccharide (LPS)-stimulated AM reduced TNF-α (at 18-24 h) and increased IL-10 (at 72-96 h) production at both protein and mRNA levels in a concentration- and time-dependent manner; and significantly reduced the TNF-α/IL-10 ratio produced by LPS-stimulated AM - demonstrating its strong anti-inflammatory properties. TNF-α/IL-10 ratio was further reduced when Composition A was used in combination with budesonide or beclomethasone - indicating it potentiates the effects of other anti-inflammatory agents. |
| Effects of Composition A on Anti-inflammatory Functions of Isolated Human Blood Neutrophils | N/A (0.2% highest Conc)- | In isolated human neutrophils stimulated by A23187 ionophore, Composition A pretreatment showed: A 75% reduction in leukotrienes at the highest dose (0.2%), as well as a 85% reduction in superoxide anion, and 50% inhibition of neutrophil degranulation. In addition, Composition A decreased the production of IL-1β and IL-8; and inhibited 5-lipooxygenase (LO) enzyme, phagocytosis and intracellular calcium mobilization. These effects may reveal the important mechanisms of Composition A's anti-inflammatory properties. |
| Composition A, a Novel Modulator of Pro- and Anti-inflammatory Cytokine Production: Effect on Th1/Th2 Cytokine Profile. | N/A (0.05 to 0.1% - low; 0.2% - high Conc.) | In isolated human peripheral blood mononuclear leucocytes (PBML): Composition A alone at low concentrations (0.05%) increased the spontaneous production of the Th2 cytokines - IL-5 and IL-13; and TNF-α production by 937 monocytoid cells at 0.1% concentration. At the higher 0.2% concentration, Composition A inhibited the spontaneous and stimulated generation of both Th1 and Th2 cytokines. These results suggest that at higher concentrations, Composition A could modulate the abnormal deviation between the Th1 and Th2 cytokines generated by immune cells in pathologic conditions. |

TABLE 8-continued

Summary of In Vitro and In Vivo Pharmacology Studies Conducted with Comp. A

| Title of Study | Formulation/Route | Results/Findings |
|---|---|---|
| \multicolumn{3}{c}{In Vivo Studies} | | |
| Correction of Cytokine Imbalance By Composition A in Dextran Sulfate Sodium (DSS)-Induced Colitis in Rats | Intrarectal (IR) and Intraperitoneal (IP) (2.5 & 5 mg/kg doses) | Composition A attenuated DSS-induced colitis in rats, reflected by a dramatic 75% reduction of colon weight-to-length ratio at the 2.5 mg/kg dose, regardless of whether administered IR or IP. The reduced inflammation was correlated with reduction in mucosal TNF-α (30% & 50% for the 2.5 & 5 mg/kg Composition A doses, respectively) and IL-1β levels (64% & 68% for the 2.5 & 5 mg/kg Composition A doses, respectively) compared to untreated rats. A significant 75% and 50% reduction in the plasma TNF-α and IL-1β levels, respectively, was also observed. |
| Correction of Cytokine Imbalance By Composition A in 2, 4, 6, Trinitrobenzene Sulfonic Acid (TNBS)-Induced Colitis in Rats | Intrarectal (IR) and Intraperitoneal (IP) (2.5 mg/kg dose) | Pretreatment with Composition A - 2.5 mg/kg IR or IP reduced weight/length ration of the colon by 33% compared to a 50% increase in the non-treated (saline) rats. A 65% reduction in the macroscopic score used to assess colonic mucosal damage was also observed. As in the DSS-induced colitis model, similar results were obtained by the IR or IP routes. |
| Anti-inflammatory Effect of Composition A in the Rat Paw Edema Model (Carrageenan Model) | Intraperitoneal (IP) (0.5, 5 & 50 mg/kg doses) and Oral (50 mg/kg dose) | Intraperitoneal Composition A pretreatment and administration simultaneously with carrageenan injection into the right paw of rats dose-dependently reduced paw thickness - 70% reduction with 50 mg/kg dose and 60% reduction with the 5 mg/kg dose. Similar results were obtained with the oral Composition A - 50 mg/kg dose compared to the IP route of administration - suggesting a high oral bioavailability of Composition A. |
| Anti-inflammatory Effects of Composition A in Transgenic Rats Expressing HLA-B27 With Spontaneous Inflammatory Disease | Oral (50 mg/kg dose)- | In transgenic rats expressing HLA-B27 phenotype and followed for 45 weeks until they developed a full-blown inflammatory disease, Composition A - 50 mg/kg administered in a single oral dose daily for 8 weeks: Significantly reduced fecal blood, an index of colitis; reduced psoriatic plaques; and increased body weight in all animals. However, it is noteworthy that the study was not well-controlled. |
| Evaluation of the Immunogenicity and Cytotoxicity of Composition A | Oral (up to 50 mg/kg in rats) Cream/Topical (5% in mice & man) (1% in albino rabbits) | Composition A did not induce any IgE immune response. No cytotoxicity was observed at doses up to Composition A - 50 mg/kg (oral liquid) in rats; following topical administration of 5% Composition A cream in mice and man; and Composition A cream 1% in albino rabbits. |

TABLE 9

Summary of Safety Pharmacology and Toxicology Studies Conducted With Comp. A

| Study Title | Results/Findings |
|---|---|
| \multicolumn{2}{c}{Safety Pharmacology Studies} | |
| A Respiratory Safety Pharmacology Study in Conscious Sprague-Dawley Rats following a Single Oral Administration. | No treatment-related adverse effects on respiratory functioning or clinical condition. |
| A Functional Observational Battery (FOB) Neurological Assessment in the Sprague- Dawley Rat Following a Single Oral Administration. | No treatment-related pharmacologically significant effect on the behavior of rats. |
| \multicolumn{2}{c}{ICH Battery of 3 Genetic Toxicology Studies} | |
| Bacterial Mutagenicity Assay (AMES Test). In-Vitro Mammalian Chromosomal Aberration Test. In-Vivo Mouse Micronucleus Test. | All 3 studies were negative - indicating Composition A was not mutagenic, did not cause any chromosomal aberrations, and was not genotoxic, respectively. |
| \multicolumn{2}{c}{Reproductive Toxicology Studies} | |
| Oral Gavage Developmental Toxicity Study in the Hannover Wister Rat (Segment II). Oral Gavage Dose Range Finding Developmental Toxicity Study in the Rabbit (Segment II). Oral Gavage Development Toxicity Study in the Rabbit (Segment II). | In all 3 studies, Composition A administration was not associated with any maternal or fetal toxicity or teratogenic effects. |

TABLE 9-continued

Summary of Safety Pharmacology and Toxicology Studies Conducted With Comp. A

| Study Title | Results/Findings |
|---|---|
| General Toxicology Studies - Oral in Rats | |
| A Maximum Tolerated Dose and 21-Day Range-Finding Oral Toxicity Study in Sprague Dawley Rats. 6-Month Oral Gavage Toxicity Study in Sprague-Dawley Rats. | All doses were well tolerated. No maximum tolerated dose was identified in the dosage range tested. No treatment-related deaths, clinical signs or findings, organ weight differences, gross morphologic or histopathological findings. |
| General Toxicology Studies - Oral in Minipigs | |
| Oral Single-Dose (Dose Range Finding) and 14-Day Repeat-Dose Exploratory Toxicity Study in Minipigs. 3-Month Oral Repeat-Dose Toxicity Study in Minipigs. | All doses were well tolerated. No maximum tolerated dose was identified in the dosage range tested. No treatment-related deaths, clinical signs or findings, organ weight differences, gross morphologic or histopathological findings. |
| General Toxicology Studies - Intrarectal in Minipigs | |
| An Intrarectal Single-Dose (Dose Range Finding) and 14-Day Repeat-Dose Exploratory Toxicity Study in Minipigs. 12-Week Intrarectal Repeat-Dose Toxicity Study in Minipigs Followed by a 2-Week Recovery Period. | All doses were well tolerated. No maximum tolerated dose was identified in the dosage range tested. No treatment-related deaths, clinical signs or findings, organ weight differences, gross morphologic or histopathological findings. |
| General Toxicology Studies - Dermal in Minipigs | |
| 5-Day Non-Occluded Exploratory Dermal Toxicity Study in Minipigs. 28-Day Non-Occluded Dermal Toxicity in Gottingen Minipigs | No treatment-related deaths or clinical signs of systemic toxicity or local reaction (edema or erythema), macroscopic or microscopic findings at all concentrations tested. |

Example 4—Phase 1 Clinical Trials

Following the positive results obtained with Composition A in preclinical studies, it was decided to begin developing it as a treatment for active mild-to-moderate distal ulcerative colitis. This led to the conduct of the first-in-man clinical trial in Germany, a Phase I safety clinical trial in normal human volunteers. We therefore submitted a clinical trial application (CTA) to Germany's federal regulatory authority—The Federal Institute for Drugs and Medical Devices (BfArM) and obtained the necessary approval.

The Phase 1 study was a randomized, double-blind, parallel-group, single-ascending dose, placebo-controlled safety and tolerability study performed in 24 healthy human volunteers assigned to four different cohorts. The doses ranged from 187.5 mg/60 g to 1500 mg/60 g of rectal enema or placebo.

The study showed no clinically relevant changes in vital signs (blood pressure, pulse rate, body temperature and respiratory rate) or electrocardiogram (ECG), no clinically significant abnormalities, no adverse events deemed related to the investigational medicinal product, and no signs of ulceration, erosion, or edema in the rectal mucosa when sigmoidoscopies were performed 8 to 10 hours after dosing.

Our conclusions from this study were as follows: Administration of up to 1500 mg/60 g of Composition A rectal enema was safe and very well tolerated. There were no clinically significant findings in any measurements, and no clinically relevant changes were observed from the pre-dose to the post-dose examinations. In addition, a maximum tolerated dose was not identified in the dosage range studied.
Safety Evaluation
Extent of Exposure
All 24 subjects included in the study received a single dose of Composition A rectal enema or placebo: eight subjects were treated with placebo; four subjects each received a single dose of 187.5 mg, 375 mg, 750 mg or 1500 mg Composition A rectal enema.

Brief Summary of Adverse Events
None of the subjects reported baseline AEs and only one subject out of the 24 subjects included in the study (4.2%) reported one AE after treatment.
Analysis of Adverse Events
For Subject 004 (placebo) a mild thrombophlebitis was reported which started on Day 3 and resolved completely within 8 days. Relationship to the study medication was rated as unrelated by the investigator.
Deaths, Other Serious Adverse Events and Other Significant Adverse Events
There were no deaths, or SAEs or other significant AEs. None of the subjects dropped out from the study due to an AE.
Clinical Laboratory Evaluation
Listings of Individual Laboratory Measurements by Subject and Each Abnormal Laboratory Value
Evaluation of Each Clinical Laboratory Parameter
Clinical Laboratory Values Over Time
Most clinical laboratory values were within the normal range. Individual deviations from the normal range were seen for a number of parameters. Most of these deviations were normal fluctuations usually observed in healthy subjects (very slight deviations from the normal range, mostly within the accuracy of the method, often already present prior to study drug administration).
A decrease in hemoglobin and hematocrit was observed in several subjects; this can be attributed to the numerous blood samplings performed in this study.
On examining the differential blood count abnormal values were seen above and below the normal range without any consistent treatment-related changes. However, it should be taken into account that the differential blood count is known to be very susceptible to artifacts.
Subject 024 (1500 mg) showed an isolated increase in AST from 28.6 U/L at screening and 34.2 U/L at check-in on Day 1 to a maximum of 72.8 U/L on Day 3 (normal range ≤48 U/L). Thereafter, AST decreased and was again within the normal range on Day 8 (47.0 U/L). No other liver function parameters showed any increase. The increase was less than twice the upper limit of the normal range and was considered as not clinically significant by the investigator. No other subject showed any remarkable changes in liver function parameters.

Stool investigations for parasites, ova, bacterial culture and toxins were all negative. All haemoccult tests were negative.

Individual Clinically Significant Abnormalities

There were no clinically significant clinical laboratory test results.

Vital Signs, Physical Findings and Other Observations Related to Safety

Blood Pressure and Pulse Rate

Mean vital sign measurements are displayed in FIG. 3 A-E.

There were no clinically significant time- or dose-related changes in mean vital signs. Overall, mean vital signs decreased after dosing in all treatment groups, which can be attributed to diurnal changes (dosing performed in the evening at bedtime).

There were some abnormal individual values outside the normal range, but the frequency of abnormal values did not increase with dose. For most parameters, values below and above the normal range were seen; the lowest frequency of abnormal values was observed after the highest dose of Composition A, except for pulse rate, where four low values were detected in subjects in the 1500 mg group (all observed in subject 019: 40 to 43 beats/min at 0.25 to 1 hour after dosing; the subject had already 42 beat/min at check-in) compared to 0 to 1 beat/min change from the pre-dose value in the other treatment groups. Most abnormal values were observed for respiratory rate, but for young healthy subjects a respiratory rate below 15/min at rest is not uncommon.

Example 5—Phase 2a Clinical Trial

Next, after receiving approval from the German regulatory authority for the first-in-patient (Phase 2a) study, we conducted a two-week, exploratory randomized, double-blind, parallel-group, dose-ranging, placebo-controlled safety, tolerability, biomarker and efficacy clinical study of Composition A rectal enema in patients with active mild-to-moderate distal ulcerative colitis.

Findings from this short, two-week study can be summarized as follows. The primary objective of this study was met. Administration of 250 mg, 500 mg and 1000 mg doses of Composition A rectal enema once daily was safe and well tolerated in subjects with active mild-to-moderate distal ulcerative colitis. These results are consistent with the results of the preceding Phase 1 study, in which single ascending doses of Composition A rectal enema from 187.5 to 1500 mg were safely and tolerably administered to healthy volunteers and a maximum tolerated dose was not observed.

The following sections present some of the important results of Composition A treatment in patients with active mild-to-moderate distal ulcerative colitis, as observed in the Phase 2a study.

Efficacy Results

Figure 4:
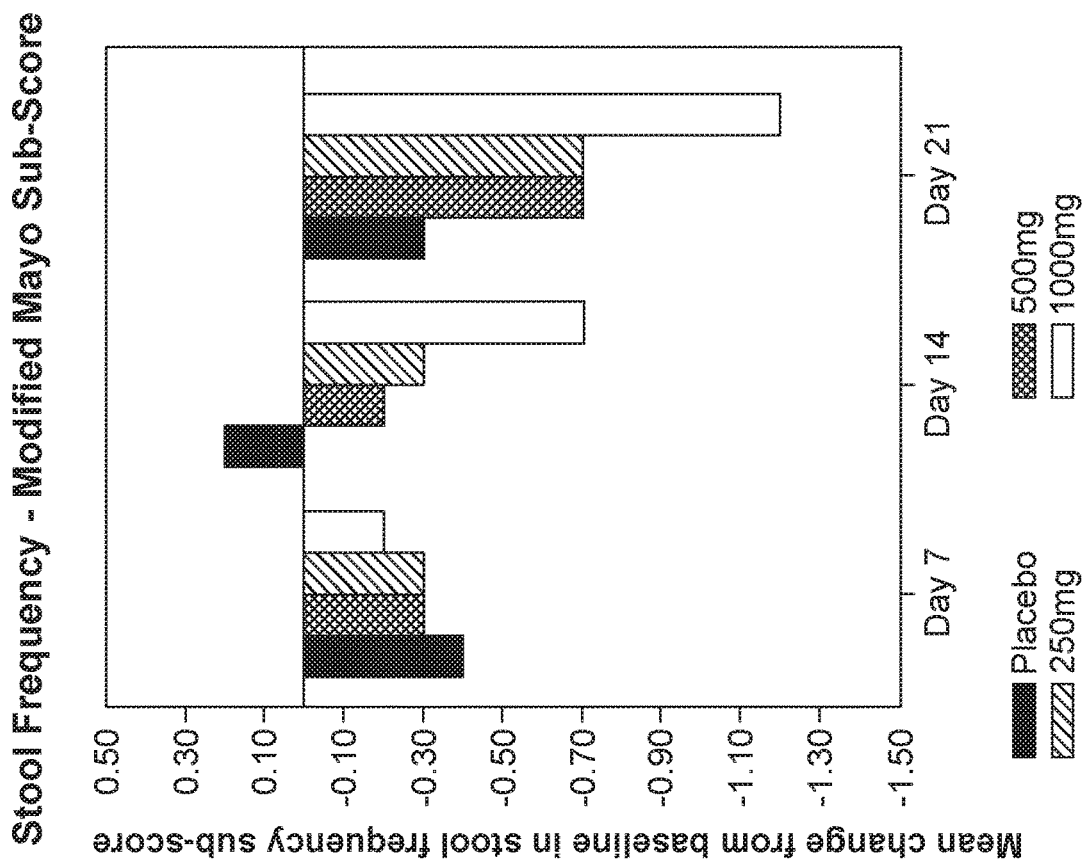
FIG. 4. Mean change from baseline in modified Mayo sub-scores in patients with active mild-to-moderate distal ulcerative colitis. A) Rectal bleeding; B) stool frequency.
Figure 4:
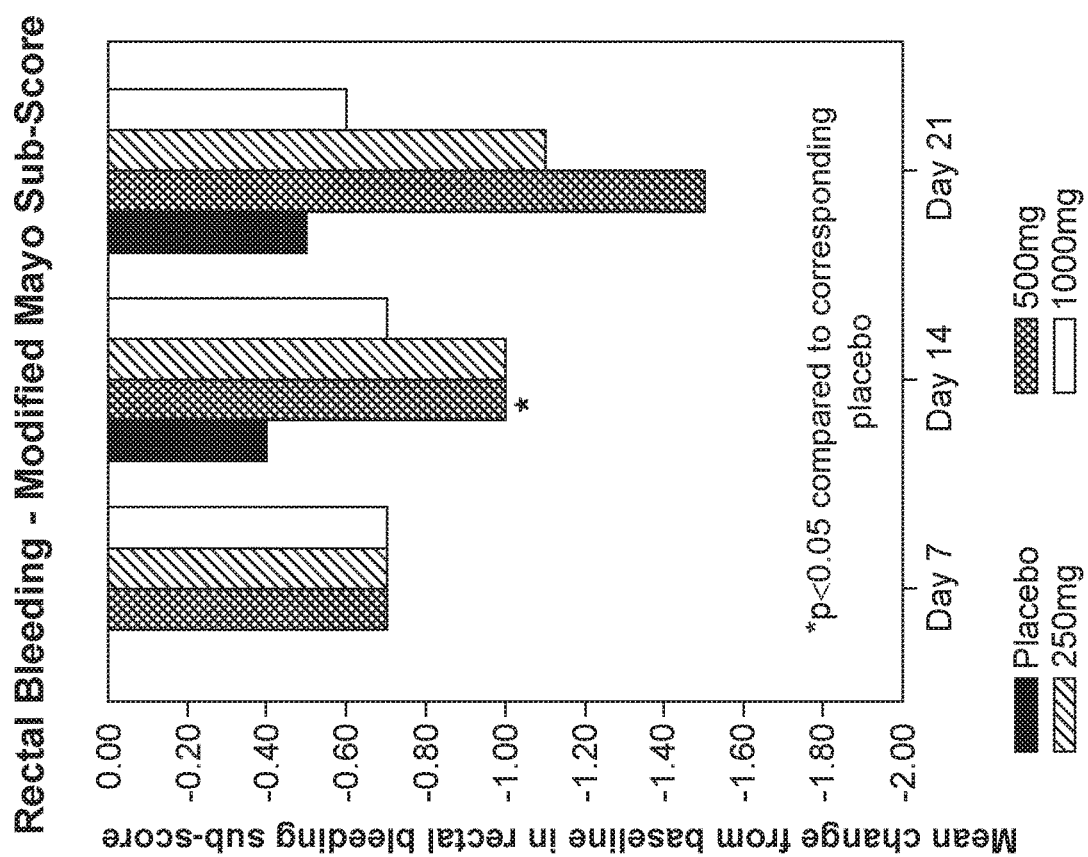

There was a statistically significant ($p<0.05$) reduction in the change from baseline in the rectal bleeding sub-score of the modified Mayo score (FIG. 4), a cardinal symptom/sign of ulcerative colitis, for the Composition A—250 mg dose compared to placebo at endpoint (Day 14). This result is particularly important because the study was not powered to detect clinically meaningful differences between the treatment groups and the 2-week duration of treatment was very short. The statistically significant placebo-corrected improvement of approximately 1-point in the rectal bleeding sub-score of the modified Mayo score, a cardinal symptom/sign of ulcerative colitis, represents a shift of severity from moderate at baseline to mild at endpoint for the Composition A-250 mg dose. This result confirms the biological activity of Composition A in active mild-to-moderate distal ulcerative colitis.

In addition, trends towards the superiority of Composition A rectal enema 500 mg and 1000 mg over placebo at endpoint were observed in the mean reductions in the two cardinal symptoms of ulcerative colitis, rectal bleeding and stool frequency sub-scores of the modified Mayo score, respectively. However, these results did not achieve statistical significance because the sample size was small but the results are suggestive of the biological activity of Composition A.

Figure 5:
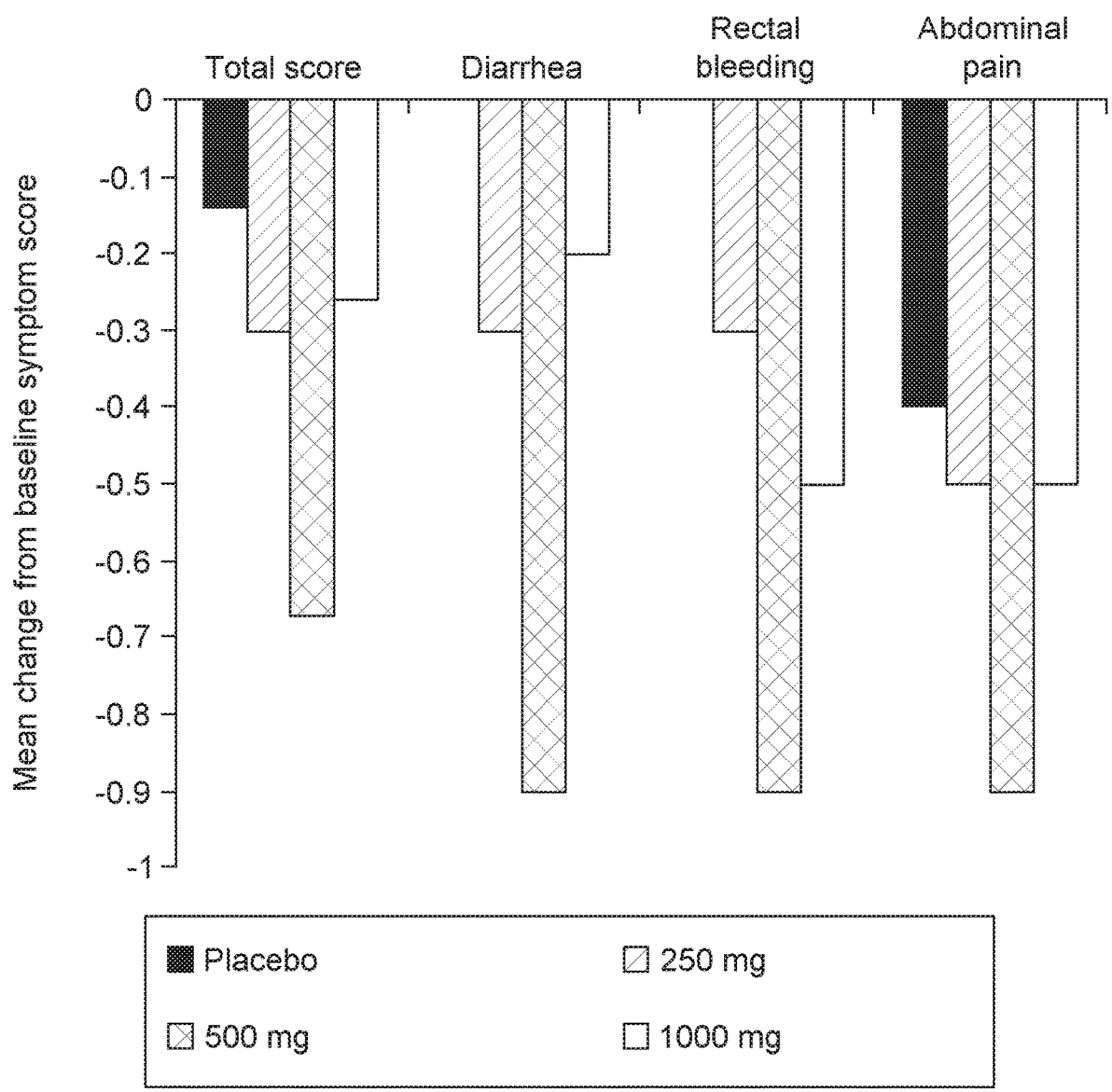
FIG. 5. Mean change from baseline in the total and symptom scores of the Investigator's Assessment of Ulcerative Colitis Symptom Score.

Similarly, a consistent trend suggesting the superiority of Composition A rectal enema (500 mg) over placebo was observed in the mean reductions in the ulcerative colitis symptom scores (rectal bleeding, diarrhea, abdominal pain, and total) by the Investigator Assessment of Ulcerative Colitis Symptom Score (FIG. 5). Again, the placebo-corrected improvements of approximately 1-point observed represent a shift of symptom severity, with the 500 mg dose for these symptoms (rectal bleeding, diarrhea and abdominal pain), from moderate at baseline to mild at endpoint. These results are also further suggestive of the drug's biological activity.

Biomarker Results

Figure 6:
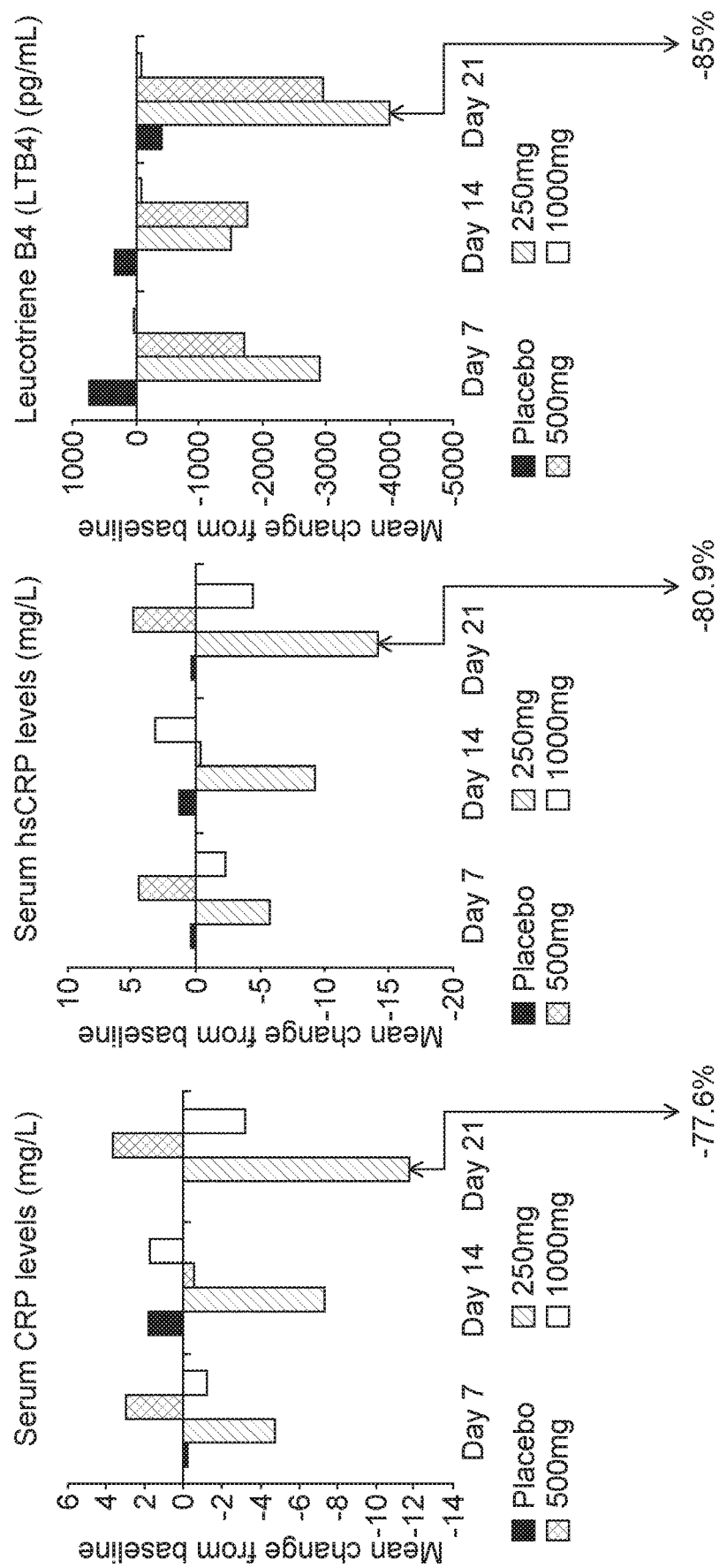
FIG. 6. Mean change from baseline in the levels of inflammatory biomarkers in patients with active mild-to-moderate distal ulcerative colitis.

As shown in FIG. 6, marked, consistent biomarker reductions of 29 to 63.6% in serum C-reactive protein ("CRP"), serum high sensitivity-CRP ("hs-CRP"), erythrocyte sedimentation rate ("ESR"), fecal calprotectin ("FC"), and fecal lactoferrin ("FL"), were observed in response to 2 weeks of Composition A 250 mg treatment (at endpoint), along with further reductions to 77.6, 80.9 and 82.9%, respectively, in CRP, hs-CRP and FL levels (250 mg: $p<0.03$; 1000 mg: $p<0.04$) by Day 21, compared with overall 18.8 to 120% increases in the placebo group over the 21 days. These marked consistent biomarker reductions are objective evidence of the drug's biological activity on intestinal inflammation in ulcerative colitis.

Further objective evidence of the biological activity of Composition A rectal enema on intestinal inflammation in ulcerative colitis included marked reductions in serum Leukotriene $B_4$ ("$LTB_4$") levels in the Composition A 250-mg treatment group. At the Day 14 visit, the levels were reduced by 31.4%, while those in the placebo group had risen by 29%. (By Day 21, the levels in the Composition A-250 mg treatment group had fallen by 85.0%.). Smaller reductions in serum $LTB_4$ levels were also observed in the 500 mg and 1000 mg Composition A treatment groups (28.0% and 22.2%, respectively). These findings are consistent with the results of earlier animal pharmacology studies which demonstrated that Composition A reduces the production and release of lipid mediators of inflammation, including prostaglandins and leukotrienes.

Figure 7:
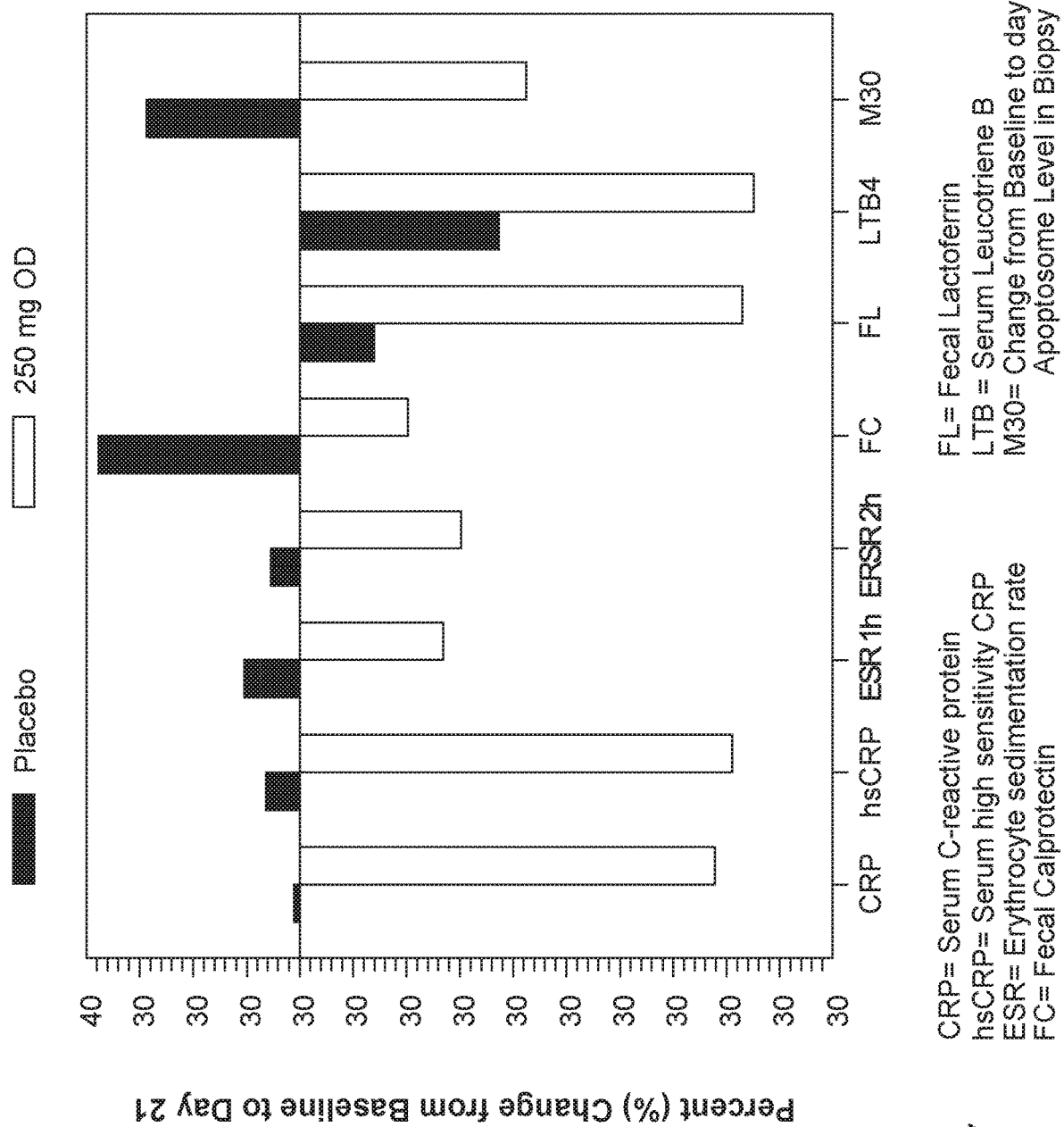
FIG. 7. Mean change from baseline in the levels of inflammatory and ulcerative colitis biomarkers (hsCRP, M30 apoptosome, etc.) 7 days after termination of treatment with Composition A—250 mg (once daily for 14 days).

Yet more objective evidence of Composition A's biological activity was demonstrated by the 42.5% reduction in the concentration of M30 apoptosome (a biomarker of apoptosis) in colonic mucosal biopsy tissue from patients receiving 250 mg and 500 mg treatments of Composition A, compared with an increase of 28.6% in the placebo group (FIG. 7).

The lack of a dose-response in the results obtained for the measured efficacy and biomarker parameters is consistent with the results obtained previously in studies conducted with approved first-line treatments for mild-to-moderate distal UC—the rectal and oral 5-aminosalicylates as well as the biologicals (for moderate-to-severe UC)—that did not also demonstrate a consistent dose-response relationship.

The data presented herein indicate that the thylakoid extract (Composition A drug substance) of the invention is active against ulcerative colitis. Interestingly, in addition, two biomarkers that have a high sensitivity and specificity to detect intestinal inflammation: fecal lactoferrin and fecal calprotectin, and two biomarkers of general inflammation the C-reactive protein (CRP) and high sensitivity C-reactive protein (hsCRP) were also markedly decreased upon treatment (see FIG. 7).

Safety Results

Administration of all 3 doses of Composition A rectal enema (250 mg, 500 mg and 1000 mg) once daily was safe and well tolerated in subjects with active mild-to-moderate distal ulcerative colitis. Overall, there were no treatment-related or serious adverse events or deaths during the study, no withdrawals due to adverse events, and there were no clinically relevant time- or treatment-related changes in the laboratory parameters, ECGs and vital signs.

Conclusions

The excellent safety profile of Composition A rectal enema to-date in both the Phase 1 and Phase 2a studies conducted, the significant reduction in rectal bleeding—a cardinal symptom of ulcerative colitis—and fecal lactoferrin levels, the marked but statistically insignificant reductions in the levels of other established biomarkers of inflammation, the exploratory biomarkers of inflammation and apoptosis (leucotriene $B_4$ and M30 apoptosome), and the trends toward superiority over placebo observed in the relief of the other key symptoms of ulcerative colitis all suggest that Composition A is active in the treatment of ulcerative colitis, and more generally inflammatory bowel disease.

Example 5—Alternative Modes of Administrations for Compliance Issues

Of course, intra-rectal administration of any drug compound may become problematic for compliance purposes when the patient has to take the medication on a long term basis. One way to diminish the impact of this mode of administration would be to administer the drug substance locally (i.e. intra-rectal: enema or suppository) upon flare-ups of the disease in order to quickly address symptoms such as pain and bleeding. The patient may be put on a maintenance dose for prevention of relapse using an oral administration that poses less compliance issues.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

All patents, patent applications and publications mentioned in this specification are herein incorporated by reference to the same extent as if each independent patent, patent application, or publication was specifically and individually indicated to be incorporated herein by reference.

REFERENCES

Bissonnette et al., 2004; *PCT-233, a novel modulator of pro- and anti-inflammatory cytokine production*, Clin Exp Immunol. 435: 440-447.

Maxwell K. (2000); *Chlorophyl fluorescence—a practical guide*. J Exp Bot. 51: 658-668.

The invention claimed is:

1. A method for treating inflammatory bowel disease (IBD) in a human subject in need thereof, comprising intrarectally administering to said subject a therapeutically effective daily dose of less than 500 mg of an active thylakoid extract comprising purified functional photosynthetic pigments in their thylakoid membrane environment, wherein said treatment decreases a baseline level of serum C-reactive protein (CRP), serum high-sensitivity C-reactive protein (hsCRP), and/or fecal lactoferrin (FL) in said subject after 14 days of administration, wherein said baseline level of CRP, hsCRP, and/or FL is measured prior to said administration.

2. The method of claim 1, wherein said extract is stabilized in a medium comprising less than 10% of electron donor.

3. The method of claim 2, wherein said medium comprises less than 10% of water.

4. The method of claim 1, wherein said thylakoid extract is in admixture with a physiologically acceptable carrier suitable for intrarectal administration.

5. The method of claim 1, wherein said IBD is selected from ulcerative colitis and Crohn's disease.

6. The method of claim 1, wherein said IBD is ulcerative colitis.

7. The method of claim 1, wherein said extract is comprised in an enema solution.

8. The method of claim 1, wherein said extract is comprised in a suppository.

9. The method of claim 1, wherein said treatment decreases the baseline level of serum C-reactive protein (CRP), serum high-sensitivity C-reactive protein (hsCRP), and/or fecal lactoferrin (FL) in said subject by at least 20% after 14 days of administration.

\* \* \* \* \*